Figure 1:
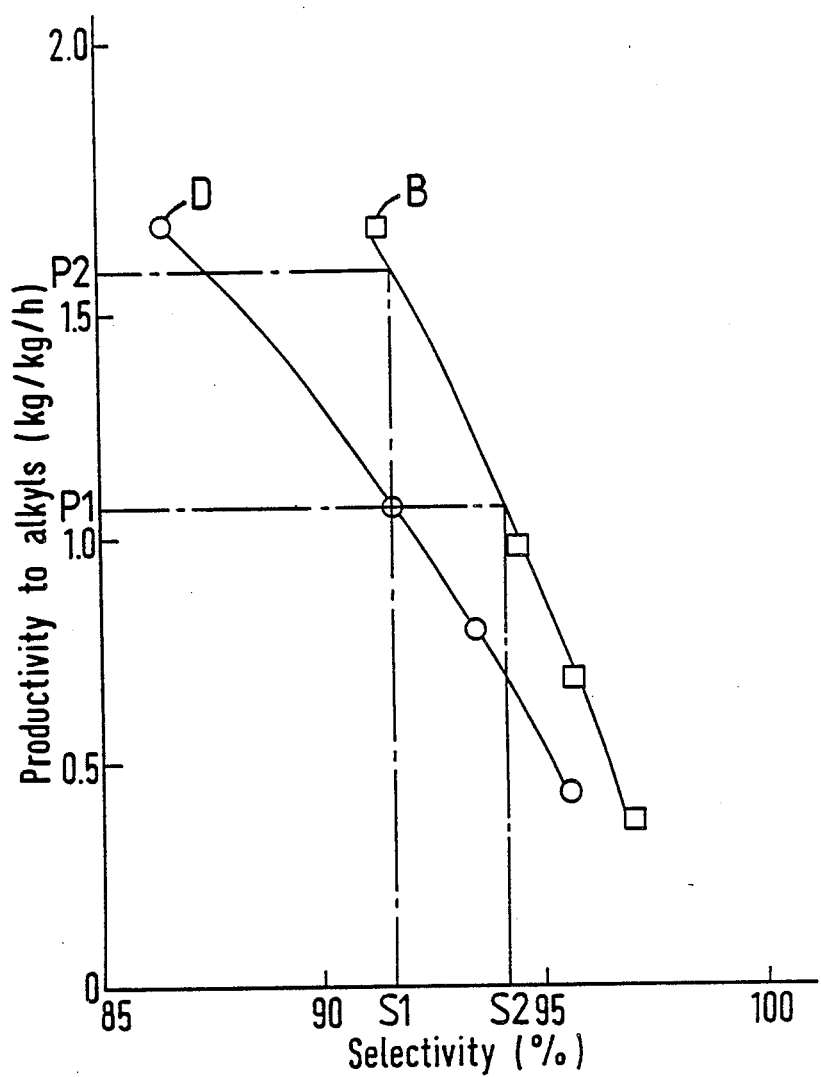

United States Patent [19]

Kitson et al.

[11] Patent Number: 4,985,572

[45] Date of Patent: Jan. 15, 1991

[54] CATALYZED HYDROGENATION OF CARBOXYLIC ACIDS AND THEIR ANHYDRIDES TO ALCOHOLS AND/OR ESTERS

[75] Inventors: Melanie Kitson; Peter S. Williams, both of Hull, England

[73] Assignees: The British Petroleum Company, p.l.c.; BP Chemicals Limited, London, both of England

[21] Appl. No.: 282,312

[22] PCT Filed: Mar. 30, 1988

[86] PCT No.: PCT/GB88/00241

§ 371 Date: Nov. 21, 1988

§ 102(e) Date: Nov. 21, 1988

[87] PCT Pub. No.: WO88/07515

PCT Pub. Date: Oct. 6, 1988

[30] Foreign Application Priority Data

Mar. 31, 1987 [GB] United Kingdom ............... 8707595

[51] Int. Cl.$^5$ ............... C07D 307/20; C07C 31/125; C07C 67/08
[52] U.S. Cl. ............... 549/326; 568/814; 568/885; 560/105; 560/265
[58] Field of Search ............... 568/814, 885; 549/326; 560/105, 265

[56] References Cited

U.S. PATENT DOCUMENTS

| | | | |
|---|---|---|---|
| 4,096,156 | 1/1978 | Freudenberger et al. | 549/326 |
| 4,104,478 | 1/1978 | Trivedi | 568/885 |
| 4,105,674 | 8/1978 | De Thomas et al. | 549/326 |
| 4,524,225 | 1/1985 | Qualeatti et al. | 568/885 |
| 4,777,303 | 10/1988 | Kirtson et al. | 568/885 |
| 4,804,791 | 2/1989 | Kirtson et al. | 568/885 |

FOREIGN PATENT DOCUMENTS

| | | | |
|---|---|---|---|
| 0174219 | 7/1985 | European Pat. Off. | 568/885 |
| 0198681 | 10/1986 | European Pat. Off. | 568/885 |
| 0198682 | 10/1986 | European Pat. Off. | 568/885 |
| 1551741 | 4/1976 | United Kingdom . | |
| 1534232 | 2/1977 | United Kingdom . | |

*Primary Examiner*—Richard L. Raymond
*Assistant Examiner*—Mark W. Russell
*Attorney, Agent, or Firm*—Brooks Haidt Haffner & Delahunty

[57] ABSTRACT

An alcohol and/or a carboxylic acid ester is produced from a carboxylic acid or anhydride thereof by reacting the acid or anhyride with hydrogen at elevated temperature in the presence as catalyst of a composition comprising an alloy of (i) at least one noble metal of Group VIII of the Periodic Table and (ii) at least one metal capable of alloying with the Group VIII noble metal, optionally including a support and at least one of the metals rhenium, tungsten or molybdenum. The process is particularly applicable to the hydrogenation of monobasic acids, for example acetic acid, and the hydrogenation of maleic acid or maleic anhydride to gamma-butyrolactone.

18 Claims, 4 Drawing Sheets

KEY:  D ... 2.5% Pd / 5% Re / HSAG
E ... 0.8% Ag / 2.5% Pd / 5% Re / HSAG
B ... 1.7% Ag / 2.5% Pd / 5% Re / HSAG
F ... 3.3% Ag / 2.5% Pd / 5% Re / HSAG

Alloyed palladium/rhenium/HSAG catalysts for acetic acid hydrogenation.

KEY:
D ... 2.5% Pd / 5% Re / HSAG
I ... 0.6% Cu / 2.5% Pd / 5% Re / HSAG
J ... 1.0% Cu / 2.5% Pd / 5% Re / HSAG
L ... 1.7% Au / 2.5% Pd / 5% Re / HSAG
M ... 0.5% Ni / 2.5% Pd / 5% Re / HSAG

Alloyed palladium / rhenium / HSAG catalysts for acetic acid hydrogenation.

KEY:  N ...                1.25% Pd /10% Re /HSAG
      G ... 1.7% Ag/1.25% Pd/10% Re/ HSAG
      H ... 1.7% Ag/1.25% Pd/10% Re/ HSAG
      K ... 0.5% Cu/1.25% Pd/10% Re/ HSAG

Alloyed palladium/rhenium/HSAG catalysts for acetic acid hydrogenation.

CATALYZED HYDROGENATION OF CARBOXYLIC ACIDS AND THEIR ANHYDRIDES TO ALCOHOLS AND/OR ESTERS

The present invention relates to the catalysed hydrogenation of carboxylic acids and their anhydrides to produce the corresponding alcohol and/or carboxylic acid ester and to catalysts for use in the aforesaid hydrogenations.

The hydrogenation of carboxylic acids to produce the corresponding alcohol in the presence of heterogeneous catalysts is known from, for example, U.S. Pat. Nos. 4,524,225, 4,104,478, GB-A-1534232, GB-A-1551741, DE-A-3221077 and EP-A-147219.

U.S. Pat. No. 4524225 describes the hydrogenation of $C_6$–$C_{24}$ fatty acids by contacting the fatty acid with hydrogen at 100° to 300° C. and 100 to 3000 psig in the presence of a zerovalent metal selected from Cu, Cr, Ru, Pt, Pd, Rs and mixtures thereof dispersed on a support which may be alpha, theta or titanated alumina, titania, or $AlPO_4$ or a mixture thereof.

U.S. Pat. No. 4,104,478 describes the production of $C_4$ to $C_{24}$ fatty alcohols by catalytically hydrogenating the corresponding fatty acid at 170° to 250° C. and 20 to 140 atmospheres over a catalyst system consisting of (a) 1 part wt. of activated Re, and (b) 0.25 to 1.5 parts of an extrinsic metal catalyst selected from Ru, Rh, Pt and Pd.

GB-A-1534232 describes the preparation of alcohols by catalytic hydrogenation of carboxylic acids at elevated temperature and pressure in the presence of water and/or solvents using a Pd/Re catalyst on a support, the catalyst having a Pd:Rs wt ratio of 0.01 to 5:1.

GB-A-1551741 describes the one-step preparation of 1,4-butanediol from maleic acid by hydrogenation in the presence of a catalyst containing (A) elments of Group VII, preferably Mn or Re, or their compounds, and (B) elements of Group VIII, preferably Ru, Rh, Pd, Os, Ir or Pt more preferably Pd or Pt or their compounds or mixtures thereof.

DE-A-3221077 describes the continuous production of ethanol by the hydrogenation of acetic acid at elevated pressure and temperature using a catalyst based on cobalt.

EP-A-147219, published after the priority date claimed for the subject application on an application claiming an earlier priority date, describes the hydrogenation of maleic acid using a Pd/Re/C catalyst.

Our copending European application publication No. 0198682 (BP Case No. 6347) provides a process for the production of an alcohol and/or a carboxylic acid ester from a $C_2$ to $C_{12}$ carboxylic acid by contacting the carboxylic acid at elevated temperature and pressure with hydrogen in the presence of a heterogeneous catalyst characterized in that the catalyst comprises a first component which is either molybdenum or tungsten and a second component which is a noble metal of Group VIII of the Periodic Table of the Elements.

Finally, our copending European application publication No. 0198681 (BP Case No. 5930) discloses a process for the production of either ethanol from acetic acid or propanol from propionic acid which process comprises contacting either acetic acid or propionic acid in the vapour phase with hydrogen at elevated temperature and a pressure in the range from 1 to 150 bar in the presence of a catalyst comprising as essential components (i) a noble metal of Group VIII of the Periodic Table of the Elements, and (ii) rhenium.

A problem associated with the use of heterogeneous hydrogenation catalysts in the aforesaid reactions is the co-production of unwanted alkanes, e.g. methene and ethane, by side-reactions, thereby decreasing the selectivity to desirable products.

We have now found that the problem of alkane formation can be reduced by the uss of alloyed catalysts.

Accordingly, in one aspect the present invention provides a process for the production from either a carboxylic acid or an anhydride thereof of the corresponding alcohol and/or carboxylic acid ester which process comprises reacting the carboxylic acid or anhydride thereof with hydrogen at elevated temperature in the presence as catalyst of a composition comprising an alloy of (i) at least one noble metal of Group VIII of the Periodic Table of the Elements, and (ii) at least one metal capable of alloying with the aforesaid Group VIII noble metal.

Hydrogen is commercially available on a large scale and may be used with or without further purification. A desirable purification may be removal of carbon monoxide.

The process of the invention is applicable to both carboxylic acids and carboxylic acid anhydrides. The carboxylic acid or carboxylic acid anhydride may be saturated or unsaturated. Mono-, di- or polybasic acids and their anhydride derivatives may be employed. Suitably the carboxylic acid or anhydride may contain from 2 to 12 carbon atoms.

Suitable monobasic acids include acids having the formula R-COOH wherein R is a substituted or unsubstituted aliphatic, aromatic or araliphatic group, which acids are hydrogenated to alcohols of the formula $RCH_2OH$. Suitably the group R may be a $C_2$ to $C_{12}$ alkyl group. Examples of suitable monobasic acids include acetic acid, propionic acid, butyric acid and heptanoic acid. A preferred monobasic acid is acetic acid.

As regards the catalyst composition, the noble metals of Group VIII of the Periodic Table of the Elements are palladium, platinum, rhodium, ruthenium, osmium and iridium. Of the afore%aid noble metals, palladium, rhodium and ruthenium are preferred. Metals capable of alloying with palladium include silver, gold, copper, nickel, rhodium, tin, cobalt, aluminium, manganese, gallium, iron, chromium and platinum, of which silver, gold and copper are preferred, silver being more preferred. Metals capable of alloying with ruthenium include iron, cobalt, manganese, germanium and rhenium.

Although a catalyst composition comprising an alloy of (i) at least one noble metal of Group VIII of the Periodic Table of the Elements, and (ii) at least one metal capable of alloying with the aforesaid Group VIII noble metal (hereinafter to ba designated component (A)) may be used as catalyst in the hydrogenation of monobasic carboxylic acids, it is preferred to employ a catalyst incorporating one or more further components.

It is preferred to incorporate (as component (B)) at least one of the metals rhenium, tungsten or molybdenum.

It is preferred to incorporate a support (as component (C)). Suitable supports include high surface area graphitised (HSAG) carbons, graphites, activated carbons, silicas, aluminas and silica/aluminas, of which HSAG carbons and high surface area silicas are preferred.

Particularly suitable supports are the high surface area graphitised carbons described in GB-A-2136704 which may be in powder or pellet form. The carbon is preferably in particulate form e.g. as pellets. The size of the carbon particles will depend on the type of reactor used.

The carbons are porous carbons. Carbons may be characterised by their BET, basal plans, and edge surface areas. The BET surface area is the surface area determined by nitrogen adsorption using the method of Brunauar Emmett and Tallar J. Am. Chem. Soc. 60,309 (1938). The basal plane surface area is the surface area determined from the heat of adsorption on the carbon of n-dotriacontane from n-heptane by the method described in Proc. Roy. Soc. A314 pages 473–498, with particular reference to page 489. The edge surface area is the surface area determined from the heat of adsorption on the carbon of n-butanol from n-heptene as disclosed in the Proc. Roy. Soc. article mentioned above with particular reference to page 495.

The carbons for use in the present invention have a BET surface area of at least 100 m$^2$/g, more preferably at least 200 m$^2$/g, most preferable at least 300 m$^2$/g. The BET surface area is preferably not greater than 1000 m$^2$/g, more preferably not greater than 750 m$^2$/g.

The ratio of BET to basal plane surface area is preferably not greater an 4:1, more preferably not greater than 2.5:1. It is particularly preferred to use carbons with ratios of BET to basal plane surface area of not greater than 1.5:1.

It is preferred to use carbons with ratios of basal plane surface area to edge surface area of at least 10:1, preferably at least 50:1. It is not believed that there is an upper limit on the ratio, although in practice it will not usually exceed 200:1.

The preferred carbon support may be prepared by heat treating a carbon-containing starting material. The starting material may be an oleophilic graphite e.g. prepared as disclosed in GB 1,168,785 or may be a carbon black.

However, oleophilic graphites contain carbon in the form of very fine particles in flake for ⓒand are therefore not very suitable materials for use as catalyst supports. We prefer to avoid their use. Similar considerations apply to carbon blacks which also have a very fine particle size.

The preferred materials are activated carbons derived from vegetable materials e.g. coconut charcoal, or from peat or coal or from carbonizable polymers. The materials subjected to the heat treatment preferably have particle sizes no less than those indicated above as being preferred for the carbon support.

The preferred starting materials have the following characteristics: BET surface area of at least 100, more preferably at least 500 m$^2$/g.

The preferred heat treatment procedure for preparing carbon supports having the defined characteristics, comprise successively(1) heating the carbon in an inert atmosphere at a temperature of from 900° C. to 3300° C., (2) oxidizing the carbon at a temperature between 300° C. and 1200° C., (3) heating in an inert atmosphere at a temperature of between 900° C. and 3000° C.

The oxidation step is preferably carried out at temperatures between 300° and 600° C. when oxygen (e.g. as air) is used as the oxidising agent.

The duration of the heating in inert gas is not critical. The time needed to heat the carbon to the required maximum temperature is sufficient to produce the required changes in the carbon.

The oxidation step must clearly not be carried out under conditions such that the carbon combusts completely. It is preferably carried out using a gaseous oxidizing agent fed at a controlled rate to avoid over oxidation. Examples of gaseous oxidising agents are steam, carbon dioxide, and gases containing molecular oxygen e.g. air. The oxidation is preferably carried out to give a carbon weight loss of at least 10% wt. based on weight of carbon subjected to the oxidation step, more preferably at least 15% wt.

The weight loss is preferably not greater than 40% wt. of the carbon subjected to the oxidation step, more preferably not greater than 25% wt of the carbon.

The rate of supply of oxidizing agent is preferably such that the desired weight loss takes place over at least 2 hours, more preferably at least 4 hours.

Where an inert atmosphere is required it may be supplied by nitrogen or an inert gas.

Preferred silica supports are those having a high surface area, typically greater than 50 m$^2$/g.

Suitably the catalyst composition comprises from 0.1 to 20% by weight, preferably from 1 to 10% by weight of component (A), from 0.1 to 20% by weight, preferably from 1 to 10% by weight of component (B), the remainder of the catalyst comprising a support.

The catalyst composition may be further modified by incorporation of a metal or metals of Group IA or Group IIA.

The alloy constituting component (A) of the catalyst composition of the present invention may be produced in any suitable manner, for example thermally or by a colloidal method. The component (A) may then be admixed with component (B). Components (A) and (B) may be applied to support either individually or in combination by conventional means.

A supported catalyst composition as hereinbefore described may suitably be produced by a process comprising the steps (i) depositing on a support at least one noble metal compound and a compound of at least one metal capable of forming an alloy with the Group VIII noble metal, said compounds being thermally decomposable/reducible to the metal, (ii) heating the composition obtained in step (i) under conditions and at a temperature such that the compounds are thermally decomposed/reduced to the metals and form an alloy thereof, and (iii) depositing on the composition obtained in step (ii) a compound of at lest one of the metals rhenium, tungsten or molybdenum.

A preferred process for producing a supported catalyst composition as hereinbefore described comprises the steps of:

(I) impregnating a support with a solution or solutions of (i) at least one soluble Group VIII noble metal compound thermally decomposable/reducible to the noble metal and (ii) a soluble compound thermally decomposable/reducible to the metal of at least one metal capable of alloying with the Group VIII noble metal and removing the solvent therefrom, (II) heating the composition obtained in step (I) under conditions and at a temperature such that the compounds are thermally decomposed/reduced to the metals and form an alloy thereof, and (III) impregnating the composition obtained in step (II) with a compound of at least one of the metals rhenium, tungsten or molybdenum and removing the solvent therefrom.

The solvent used in steps (I) and (III) of the process may be the same or different, preferably the same, and may be any suitable solvent, for example water.

Techniques for impregnating supports with solutions of metal compounds and removing the solvent therefrom are well known in the art and require no further elaboration. Such techniques include the incipient wetness technique and the excess solution technique.

In step (II) the composition may suitably be heated at a temperature above about 600° C. to thermally decompose/reduce thermally decomposable/reducible compounds of the metals to the elemental metals and produce alloys thereof. This heating step may suitably be accomplished in the presence of an inert gas, for example nitrogen. Although about 600° C. is indicative of the temperature at which palladium and silver must be heated to form the alloy, the optimum temperature will depend on the nature of the particular combination of metals involved.

Preferably, a further step is interposed between step (I) and step (II) and optionally following step (III) wherein the impregnated support is dried, suitably by heating at a temperature in the range from 50° to 150° C. It will be appreciated by those skilled in the art that this step may be incorporated into step (II), if desired.

Following step (III) there may be incorporated a further step (IV) wherein thermally decomposable/reducible compounds of at least one of the metals rhenium, tungsten or molybdenum is (are) thermally decomposed/reduced to the metallic form. Alternatively, this may be accomplished in a catalyst activation step.

Suitable molybdenum, tungsten or rhenium compounds which are decomposable/reducible to the metal and/or oxide include salts of the metals and salts wherein the metals are present in the anionic moiety, for example, ammonium molybdate or ammonium tungstate. Suitable noble metal compounds which are decomposable/reducible to the noble metal include, for example, noble metal salts such as the carboxylates, halides and nitrates and ammonium salts containing the noble metal in the anion moiety, for example ammonium tetrachloropalladate. Suitable compounds of metals capable of alloying with a noble metal include salts of the metals, for example nitrates, carboxylates and halides.

The metal of Group IA, Group IIA or Group IVA of the Periodic Table of the elements may be added to the catalyst composition at any point during its preparation. Thus, the supported alloy composition may be impregnated with a solution of a soluble compound of the metal. Alternatively, a soluble compound of the metal may be added to the impregnation solutions.

A preferred catalyst comprises (i) an alloy of palladium and silver and (II) rhenium supported on a high surface area graphitised carbon of the type described in the aforesaid GB-A-2136704.

Before use in the process of the invention the catalyst is preferably activated by contact at elevated temperature with either hydrogen or a hydrogen/inert gas, for example nitrogen mixture, suitably for a period of from 1 to 20 hours. The elevated temperature may suitably be in the range from 200° to 350° C. Alteratively, the catalyst may be activated by heating to the reaction temperature in the presence of reactants.

Using monobasic acids the process of the invention may suitably be operated at an elevated temperature in the range from 100° to 300° C., preferably from 150° to 250° C. The pressure may suitably be less then 50 bar.

The process may be operated in the liquid phase or the vapour phase.

The process may be operated batchwise or continuously, preferably continuously. The catalyst may be employed in the form of a fixed bed, a moving ted or a fluidised bed. The Gas Hourly Space Velocity for continuous operation may suitably be in the range from 50 to 50,000 $h^{-1}$, preferably from 2,000 to 30,000 $h^{-1}$.

In addition to the alcohol, the process of the invention generally also produces the corresponding ester as a by-product, for example the hydrogenation of acetic acid generally also produces ethyl acetate and the hydrogenation of propionic acid generally also produces propyl propionate. The proportion of the ester in the product will depend on the nature of the catalyst. The proportion of ester may be further increased, if desired, by feeding additional carboxylic acid and/or by introducing an acidic function into the catalyst to promote 'in situ' esterification. It is possible, therefore, to produce a product mainly comprising the carboxylic acid ester, particularly by operating in the liquid phase at low conversions, for example less than 50%.

It is an advantage of the process of the present invention that the selectivity of monobasic acid hydrogenation to desired products (alcohol/ester) can be increased at the expense of undesirable products (alkanes).

The process of the present invention is particularly applicable to the hydrogenation of dicarboxylic acids and their anhydrides, more particularly to the hydrogenation of unsaturated dicarboxylic acids and their anhydrides. Examples of suitable dicarboxylic acids and their anhydrides include glutaric acid, glutaric anhydride, adipic acid, adipic anhydride, succinic acid, succinic anhydride, maleic acid and malaic anhydride.

The hydrogenation of malaic acid or maleic anhydride to gamma-butyrolactone is generally difficult to accomplish because the gamma-butyrolacetone product generally reacts further with hydrogen to produce 1,4-butanediol and tetrahydrofuran. In addition to decreasing unwanted alkane production, the alloy catalysts of the present invention can also inhibit the further reaction of gamma-butyrolactone to by-products, for example 1,4-butanediol and tetrahydrofuran.

In another aspect therefore the present invention provides a process for the production of gamma-butyrolactone from either maleic acid or maleic anhydride which process comprises reacting either maleic acid or maleic anhydride at elevated temperature with hydrogen in the presence as catalyst of component (A) as hereinbefore described.

Component (A) preferably comprises either palladium, ruthenium or rhodium, more preferably palladium as the noble metal (i) and either silver, gold or copper, more preferably silver, as the metal (ii) capable of alloying with palladium. A particularly preferred alloy is an alloy of palladium and silver. Component (A) may be used as catalyst either with or without the Hereinbefore described components (B) and (C), though the presence of component (C), i.e. a support, is preferred. A preferred support is an HSAG carbon as hereinbefore described.

The catalyst is preferably activated before use in the process by the method as hereinbefore described.

The process may be operated batchwise or continuously and the maleic acid or anhydride may be introduced in either the liquid phase or the vapour phase. In the liquid phase it is preferred to use a solvent for the maleic anhydride. As the solvent there may be used either water or an inert organic solvent, for example 1,4-dioxane, water being a suitable solvent for malaic acid and 1,4-dioxane a suitable solvent for maleic anhydride.

As regards the reaction conditions, the temperature may suitably be in the range from 50° to 350 C., preferably 150° to 300° C., and the pressure may suitably be in the range from 1 to 300 barg, preferably 10 to 150 barg. The Liquid Hourly Space Velocity (LHSv) for continuous operation may suitably be in the range from 0.05 to 10, preferably from 0.1 to 5. The gas to liquid ratio for liquid phase operation may suitably be in the range from 1:300, preferably from 1:100.

In a final aspect the present invention provides a catalyst composition suitable for uss in the hydrogenation of carboxylic acids and their anhydrides which composition comprises components (A) and (C) as hereinbefore described.

The catalyst composition may suitably incorporate component (B) as hereinbefore described.

A particularly preferred catalyst composition comprises an alloy of palladium and silver and an HSAG carbon as hereinbefore described, optionally incorporating also rhenium.

The invention will now be further illustrated by reference to the following Examples and Comparison Tests.

In the following Examples and Comparison Tests the term "HSAG carbon" denotes high surface area graphitised carbon, prepared and characterised as follows:

The carbon used as support was prepared from a commercially available activated carbon sold by Ceca under the designation Acticarbone ACL40. The activated carbon was heat treated as follows. The carbon was heated from room temperature in a stream of nitrogen to 1700°–1800° C. over a period of about one hour. The temperature was held at 1700°–1800° C. for about twenty minutes then the carbon was cooled to room temperature. A water cooled heat exchanger was used to lower the temperature in a period of one hour. The carbon was then heated in air in a rotating kiln furnace at approximately 520° C. for a time known from experience to give a weight loss of 20% wt at a rate of less than 5% wt per hour. The carbon was then heated in nitrogen to between 1700° C. and 1800° C. and cooled to room temperature in a nitrogen atmosphere. The resulting a graphite-containing carbon was then crushed to 16–30 mesh BSS.

The resulting carbon had the following properties:

| | |
|---|---|
| BET surface area | 628 m$^2$/g |
| Basal plane surface area | 460 m$^2$/g |
| Edge surface area | 8 m$^2$/g |
| BET/basal surface area ratio | 1.36 m$^2$/g |
| Basal plane/edge surface area ratio | 58 |

The carbon was then refluxed in 5% hydrochloric acid in aqueous solution for 2–3 hours, filtered and washed with distilled water. It was refluxed in distilled water for 2–3 hours, filtered and dried overnight in a vacuum oven at 100° C.

CATALYST PREPARATION - PALLADIUM BASED CATALYSTS

In the following procedures nominal loading is defined as weight of metal (not salt) added to the support expressed as a percentage of the weight of support.

EXAMPLE 1

An aqueous solution containing dissolved palladium nitrate and silver nitrate was added to HSAG carbon. The water was removed on a rotary evaporator, and the resulting impregnated carbon was then dried at 100° C. in a vacuum overnight. The amounts of the various components were chosen to give a composition with a nominal loading as follows: 1.7% Ag, 2.5% Pd. The composition was then cooled and transferred to a glass tube, and was then heated in a stream of nitrogen using the following conditions:

from room temperature to 600° C. over a period of eight hours then eight hours at 600° C. followed by cooling to room temperature in nitrogen. The resulting catalyst composition is designated Catalyst A.

EXAMPLE 2

Catalyst A was then mixed with an aqueous solution of rhenium heptoxide, the solvent again removed on a rotary evaporator, and the composition dried overnight in a vacuum oven at 100° C. to give a catalyst of nominal loading - 1.7% Ag, 2.5% Pd, 5% Re. The resulting catalyst composition is designated Catalyst B.

Comparison Test 1

The procedure of Example 1 was repeated except that silver nitrate was omitted from the preparation and the amounts of the various components were chosen to give a composition with a nominal loading as follows 2.5% Pd. A second difference was that the composition was heated in a stream of nitrogen using the following conditions:

from room temperature to 300° C. over a period of six hours, then ten hours at 300° C. followed by cooling to room temperature in nitrogen.

The resulting catalyst composition which is not according to the present invention is designated Catalyst C.

Comparison Test 2

The procedure of Example 2 was repeated using catalyst C of Comparison Test 1 instead of Catalyst A to give a composition of the normal loading: 2.5% Pd, 5% Re.

The resulting catalyst composition which is not according to the present invention is designated Catalyst D.

Comparison Test 2A

Comparison Test 1 was repeated except that the composition was heated to 600° C. instead of 300° C. Thereafter the procedure of Comparison Test 2 was followed to give a catalyst designated as Catalyst D1.

EXAMPLES 3-6

A procedure similar to that described in Examples 1 and 2 was used to produce Ag/Pd/Re/HSAG catalysts having a range of silver loadings as follows:

Ex 3, Catalyst E - 0.8% Ag/2.5% Pd/5% Re/HSAG
Ex 4, Catalyst F - 3.3% Ag/2.5% Pd/5% Re/HSAG
and different Pd loadings as follows:
Ex 5, Catalyst G - 1.7% Ag/1.25% Pd/10% Re/HSAG Ex 6, Catalyst H - 1.7% Ag/1.25% Pd/10% Re/H-SAG Details of the preparation procedures and the catalyst compositions are shown in Table 1.

EXAMPLES 7-9

A procedure similar to that described in Examples 1 and 2 was used except that instead of silver nitrate there was used copper nitrate to produce Cu/Pd/Re/HSAG catalysts as follows:

Ex 7, Catalyst I - 0.6% Cu/2.5% Pd/5% Re/HSAG
Ex 8, Catalyst J - 1.0% Cu/2.5% Pd/5% Re/HSAG
Ex 9, Catalyst K - 0.5% Cu/1.25% Pd/10% Re/H-SAG Details of the preparative procedures and the catalyst compositions are given in Table 1.

EXAMPLE 10

A procedure similar to that described in Examples 1 and 2 was used except that instead of silver nitrate there was used gold chloride to produce a catalyst (L) having the composition:

1.7% Au/2.5% Pd/5% Rs/HSAG

Details of the preparative procedure and the composition are given in Table 1.

EXAMPLE 11

A procedure similar to that described in Examples 1 and 2 was used except that instead of silver nitrate there was used nickel nitrate to produce a catalyst (M) having the composition:

0.5% Ni/2.5% Pd/5% Re/HSAG

Details of the preparative procedure and the catalyst composition are given in Table 1.

Comparison Test 3

The procedure of Comparison Test 2 was repeated except that the relevant proportions were altered to produce a catalyst (N) having the composition:

1.25% Pd/10% Re/HSAG

Details of the preparative procedure and the catalyst composition are given in Table 1.

TABLE 1

| Ex | Catalyst | Nominal Catalyst Composition | Pd Wt % | Re Wt % | Ag Wt % | Cu Wt % | Au Wt % | Ni Wt % | Alloying Conditions |
|---|---|---|---|---|---|---|---|---|---|
| CT2 | D | 2.5% Pd/5% Re/HSAG | 1.91 | 4.6 | — | — | — | — | |
| CT2 | D1 | 2.5% Pd/5% Re/HSAG | 1.99 | 4.67 | — | — | — | — | |
| 3 | E | 0.8% Ag/2.5% Pd/5% Re/HSAG | 1.96 | 4.55 | 0.71 | — | — | — | Nitrogen, 600° C. for 8 hours with a 6-8 hour heat-up time. |
| 2 | B | 1.7% Ag/2.5% Pd/5% Re/HSAG | 1.9 | 4.3 | 1.3 | — | — | — | |
| 4 | F | 3.3% Ag/2.5% Pd/5% Re/HSAG | 1.95 | 4.54 | 2.50 | — | — | — | |
| 7 | I | 0.6% Cu 2.5% Pd/5% Re/HSAG | 1.89 | 4.1 | — | 0.58 | — | — | Hydrogen, 300° C. for 3 hours (4 hour heat-up time). Then nitrogen, 650° C. for 8 hours (6 hour heat-up time). |
| 8 | J | 1% Cu/2.5% Pd/5% Re/HSAG | 1.84 | 4.00 | — | 0.92 | — | — | |
| 10 | L | 1.7% Au/2.5% Pd/5% Re/HSAG | 1.92 | 4.3 | — | — | 1.67 | — | Hydrogen, 300° C. for 3 hours (4 hour heat-up time). Then nitrogen, 650° C. for 8 hours (6 hour heat-up time). |
| 11 | M | 0.5% Ni/2.5% Pd/5% Re/HSAG | 1.97 | 4.0 | — | — | — | 0.44 | Hydrogen, 300° C. for 3 hours (4 hour heat-up time). Then nitrogen, 700° C. for 8 hours (6 hour heat-up time). |
| CT3 | N | 1.25% Pd/10% Re/HSAG | 0.88 | 8.04 | — | — | — | — | |
| 5 | G | 1.7% Ag/1.25% Pd/10% Re/HSAG | 0.93 | 8.58 | 1.39 | — | — | — | Nitrogen, 600° C. for 8 hours with 10 hour heat-up time. |
| 6 | H | 1.77% Ag/1.25% Pd/10% Re/HSAG | 1.05 | 8.91 | 1.28 | — | — | — | |
| 9 | K | 0.5 Cu/1.25% Pd/10% Re/HSAG | | | | | | | Hydrogen, 300° C. for 3 hours (4 hour heat-up time). Then nitrogen, 650° C. for 8 hours (6 |

Alloy Catalyst Characterisation by X-Ray Diffraction

The alloys were examined by X-ray diffraction (XRD), before rhenium impregnation to determine their stoichiometries and average crystallite sizes.

The alloys and their constituents are all face-centred cubic structures and the alloys had lattice parameters between those of their parent elements. By using an internal standard to measure accurately the alloy latice parameter the composition can be estimated by interpolation assuming a linear relationship between composition and lattice parameters. In some catalysts the presence of several phases made it impossible to measure lattice parameters with sufficient accuracy to permit a composition analysis. The average crystallite size of the alloys was in the range observed for the palladium only catalysts. The data, together with catalyst compositions as measured by XRF is given in Table 2.

Palladium/Silver

Most of the palladium and silver became incorporated into an alloy and in all but one sample only one alloy was formed. The compositional information gained from XRD agreed moderately well with the composition measured by XRF.

Palladium/Copper

Some of the copper was 'invisible' to XRD suggesting that it was present as a highly dispersed or amorphous phase. The rest of the copper was incorporated into a palladium/copper alloy. One sample also contained a significant amount of palladium metal.

Palladium/Gold

This one sample contained a mixture of alloy compositions plus palladium metal. It suggests that more extreme conditions may be needed to promote better alloying and possibly a better catalyst.

Palladium/Nickel

It would appear that longer heating times and/or higher temperatures may be required to better promote the formation of nickel/palladium alloys.

Palladium/Rhenium

A catalyst similar in composition to catalyst D and prepared in a similar manner but differing only in the respect that the HSAG was heat treated differently and had slightly different properties was analysed by XRD. This catalyst contained only one crystalline phase-palladium metal with an average crystallite size greater than 100 Angstroms.

TABLE 2

| Catalyst | Nominal Composition | Molar Ratio from XRF | Alloy(s) Composition | Average Crystallite Size (A) |
|---|---|---|---|---|
| | | | X-Ray Diffraction Data | |
| E of Ex 3 | 0.8% Ag/ 2.5% Pd/ 5% Re/HSAG | 1(Pd):0.36(Ag) | Alloy 1(Pd):0.67(Ag) Alloy 1(Pd):0.27(Ag) | 115 70 |
| B of Ex 2 | 1.7% Ag/ 2.5% Pd/ 5% Re/HSAG | 1(Pd):0.67(Ag) | Alloy 1(Pd):0.92(Ag) + palladium metal (traces) | 140 |
| F of Ex 4 | 3.3% Ag/ 2.5% Pd/ 5% Re/HSAG | 1(Pd):1.26(Ag) | Alloy 1(Pd):1.38(Ag) + silver metal (traces) | 130 |
| G of Ex 5 | 1.7% Ag/ 1.25% Pd/ 10% Re/HSAG | 1(Pd):1.47(Ag) | Alloy 1(Pd):1.44(Ag) + silver metal (traces) | 85 |
| H of Ex 6 | 1.7% Ag/ 1.25% Pd/ 10% Re/HSAG | 1(Pd):1.28(Ag) | Alloy 1(Pd):1.5(Ag) + silver chloride (traces) | |
| I of Ex 7 | 0.6% Cu/ 2.5% PD 5% Re/HSAG | 1(Pd):0.51(Cu) | Palladium metal + possible evidence for alloying | 120 |
| J of Ex 8 | 1.0% Cu/ 2.5% Pd/ 5% Re/HSAG | 1(Pd):0.84(Cu) | Alloy 1(Pd):0.25(Cu) | 110 |
| K of Ex 9 | 0.5% Cu/ 1.25% Pd/ 10% Re/HSAG | | Alloy 1(Pd):0.27(Cu) | 95 |
| L of Ex 10 | 1.7% Au/ 1.25% Pd/ 5% Re/HSAG | 1(Pd):0.47(Au) | Mixture of several different Pd/Au alloys palladium metal | 150 |
| M of Ex 11 | 0.5% Ni/ 1.25% Pd/ 5% Re/HSAG | 1(Pd):0.40(Ni) | Palladium metal + some evidence for a small amount of alloying | 135 |

CATALYST TESTING (I) Hydrozenation of acetic acid

For experiments at pressures in the range 1–11 barg, 2.5 mls of catalyst was loaded into a corrosion resistant stainless steel tube of internal diameter 6–7 mm, and the reactor tube assembly placed in a tubular furnace. The catalyst was then activated by heating at atmospheric pressure in a stream of hydrogen to either 280° C. or 300° C. over a two hour period, and then holding at the final temperature for one hour. After activation, the catalyst was cooled in hydrogen to the desired reaction temperature. A mixture of carboxylic acid vapour and hydrogen was then passed over the catalyst, and pressure was adjusted to the required value by means of a back-pressure regulator. The vapour/hydrogen mixture was formed in a vapourising zone, to which acetic acid liquid and hydrogen gas were separately metered. The product vapours and gases leaving the reactor were sampled on-line and analysed by gas-liquid chromatography (glc).

The temperature was measured by means of a thermocouple inserted into the catalyst bed.

The product mixtures typically contained the appropriate alcohol and ester (the latter formed by esterification of alcohol with unreacted acid), together with traces of the appropriate dialkyl ether, and aldehyde, and by-product methane, ethane and (with propionic acid only) propane. In general, with carbon and silica supported catalysts, the main product is alcohol, especially at high conversions.

For the purposes of the Examples, conversions and selectivities have been calculated as respectively, the proportion of carboxylic acid hydrogenated, and the proportion of the hydrogenated carboxylic acid which is not converted into alkane by-product. Thus, selectivity denotes the ability of the catalyst to carry out hydrogenation without alkanation. In all examples (unless stated otherwise) only small amounts (<2%) of dialkyl ether and aldehyde are formed.

DEFINITIONS

WHSV=Weight Hourly Spacs velocity=kg liquid feed per kg catalyst per hour.

LHSv=Liquid Hourly Space Velocity=liters liquid feed per 4 liter of catalyst per hour.

Productivity to alkyls=kg acid converted to all products other than alkane by-products per kg catalyst per hour.

EXAMPLES 12-15

Acetic acid was hydrogenated over the catalyst composition B of Example 2. The WHSV was ca 3.8 (LHSV=1.34 h-1), the ratio hydrogen to acetic acid was ca 10,1 molar, and the pressure was 10.3 barg. In each case the catalyst was activated at 280° C. The results are collected in Table 3 and plotted in FIG. 1.

No deactivation was observed over run periods of up to 24 hours.

Comparison Tests 4–7

The procedure of Examples 2–5 was repeated except that catalyst composition D was used in place of catalyst composition B.

The results are collected in Table 3 and plotted in FIG. 1.

TABLE 3

| Example | Catalyst | Temperature °C. | Productivity to Alkyls (kg/kg/h) | Selectivity (%) |
|---|---|---|---|---|
| 12 | B | 249 | 1.69 | 91.4 |
| 13 | B | 231 | 0.98 | 94.5 |
| 14 | B | 215 | 0.69 | 95.7 |
| 15 | B | 194 | 0.37 | 97.0 |
| Comp Test 4 | D | 251 | 1.70 | 86.5 |
| Comp Test 5 | D | 232 | 1.07 | 91.7 |
| Comp Test 6 | D | 217 | 0.80 | 93.5 |
| Comp Test 7 | D | 196 | 0.43 | 95.6 |

The results show that alloying the palladium with silver increases the selectivity and slightly decreases the productivity to alkyls. D is included for comparison purposes and is not according to the present invention. The Figure shows the advantage to be gained by alloying the palladium with silver. By using the appropriate temperature the same productivity (P1) can be obtained at higher selectivity with B (S2 is greater than S1). Also a higher productivity can be obtained using B (P2 is greater than P1) at a constant selectivity (S2).

EXAMPLES 16 to 19

The procedure of Examples 12 to 15 was repeated except that instead of Catalyst B of Example 2 there was used Catalyst E of Example 3.

The results are presented in Table 4.

EXAMPLES 20 to 23

The procedure of Examples 12 to 15 was repeated except that instead of Catalyst B of Example 2 there was used Catalyst F of Example 4.

The results are presented in Table 4.

Comparison Tests 8 to 11

The procedure of Examples 12 to 25 was repeated except that instead of Catalyst B of Example 2 there was used Catalyst D1 of Comparison Test 2A.

The results are presented in Table 4.

TABLE 4

| | PALLADIUM/SILVER/RHENIUM/HSAG | | | | | |
|---|---|---|---|---|---|---|
| Catalyst Code | Nominal Catalyst Composition | Temperature °C. | Productivity to Ethyls (kg/kg/h) | Selectivity (%) | | |
| | | | | Ethyls | Methane | Ethane |
| D | 2.5% Pd/ | 251 | 1.70 | 86.5 | 7.9 | 5.6 |
| | 5% Re/HSAG | 232 | 1.07 | 91.7 | 4.3 | 4.0 |
| | | 217 | 0.80 | 93.5 | 3.2 | 3.3 |
| | | 196 | 0.43 | 95.6 | 1.8 | 2.5 |
| D1 | 2.5% Pd/ | 250 | 1.96 | 87.2 | 6.5 | 6.2 |
| | 5% Re/HSAG | 231 | 1.14 | 92.2 | 3.7 | 4.2 |
| | | 220 | 0.83 | 93.8 | 2.7 | 3.5 |
| | | 195 | 0.43 | 95.7 | 1.7 | 2.7 |
| E | 0.8% Ag/ | 249 | 1.82 | 88.7 | 5.4 | 5.9 |
| | 2.5% Pd/ | 231 | 1.18 | 92.7 | 3.1 | 4.2 |
| | 5% Re/HSAG | 213 | 0.78 | 94.6 | 2.2 | 3.3 |
| | | 191 | 0.37 | 96.2 | 1.4 | 2.5 |
| B | 1.7% Ag/ | 249 | 1.69 | 91.4 | 3.6 | 5.1 |
| | 2.5% Pd/ | 231 | 0.98 | 94.5 | 1.9 | 3.6 |
| | 5% Re/HSAG | 215 | 0.69 | 95.7 | 1.4 | 2.9 |
| | | 194 | 0.37 | 97.0 | 0.8 | 2.2 |

TABLE 4-continued

| | PALLADIUM/SILVER/RHENIUM/HSAG | | | | | |
|---|---|---|---|---|---|---|
| Catalyst Code | Nominal Catalyst Composition | Temperature °C. | Productivity to Ethyls (kg/kg/h) | Selectivity (%) | | |
| | | | | Ethyls | Methane | Ethane |
| F | 3.3% Ag/ | 251 | 1.77 | 90.2 | 4.5 | 5.3 |
| | 2.5% Pd/ | 231 | 1.01 | 94.2 | 2.3 | 3.5 |
| | 5% Re/HSAG | 218 | 0.78 | 95.2 | 1.8 | 3.1 |
| | | 196 | 0.41 | 96.7 | 1.0 | 2.3 |

Figure 2:
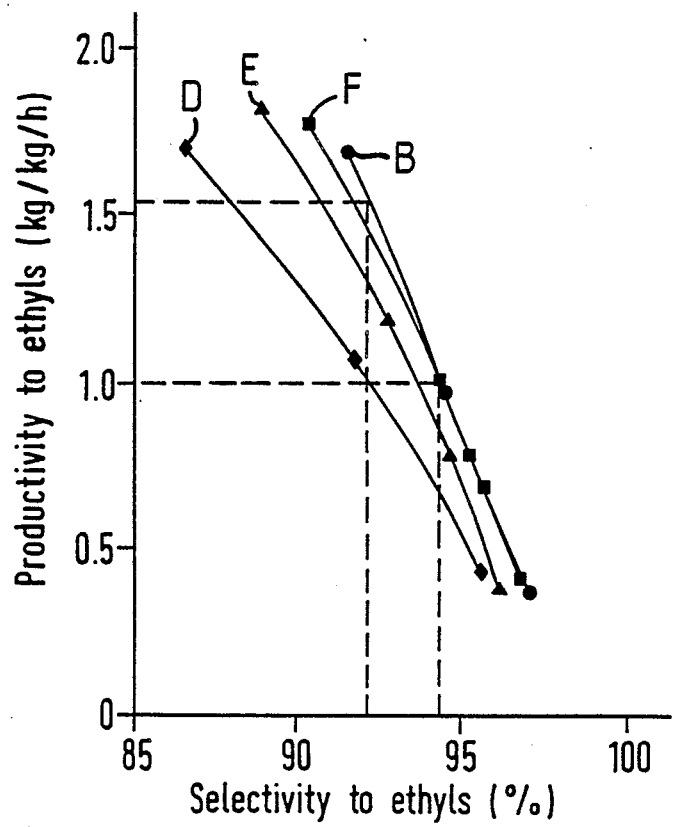

The results provided in Table 4 are presented in graphical form in FIG. 2. It can be seen from FIG. 2 that adding silver as an alloy with palladium to-the palladium/rhenium/HSAG catalyst shifts the productivity/selectivity 'operating line'. The improvements in catalyst performance can be taken in one of two ways, by choosing the appropriate operating temperature. At a productivity of 1 kg/kg catalyst/h the selectivity of the catalyst can be improved from 92% to by alloying with silver. Alternatively, at a selectivity of 92% the productivity can be improved from 1.0 to 1.6 kg/kg catalyst/h. In general there is more divergence from the operating lines, and hence more benefits from alloying, at higher temperatures, i.e. high productivities and low selectivities.

EXAMPLES 24 to 27

The procedure of Examples 12 to 15 was repeated except that instead of Catalyst B of Example 2 there was used Catalyst I of

EXAMPLE 7.

The results are presented in Table 5.

EXAMPLES 28 to 31

The procedure of Examples 12 to 15 was repeated except that instead of Catalyst B of Example 2 there was used Catalyst J of Example 8.

The results are presented in Table 5.

EXAMPLES 32 to 35

The procedure of Examples 12 to 15 was repeated except that instead of Catalyst B of Example 2 there was used Catalyst L of Example 10.

The results are presented in Table 5.

EXAMPLES 36 to 39

The procedure of Examples 12 to 15 was repeated except that instead of Catalyst B of Example 2 there was used Catalyst M of Example 11.

The results are Presented in Table 5.

TABLE 5

| | PALLADIUM/COPPER (GOLD OR NICKEL)/RHENIUM/HSAG | | | | | |
|---|---|---|---|---|---|---|
| Catalyst | Nominal Catalyst Composition | Temperature (°C.) | Productivity to Ethyls (kg/kg/h) | Selectivity (%) | | |
| | | | | Ethyls | Methane | Ethane |
| D | 2.5% Pd/ | 251 | 1.70 | 86.5 | 7.9 | 5.6 |
| | 5% Re/HSAG | 232 | 1.07 | 91.7 | 4.3 | 4.0 |
| | | 217 | 0.80 | 93.5 | 3.2 | 3.3 |
| | | 196 | 0.43 | 95.6 | 1.8 | 2.5 |
| I | 0.6% Cu/ | 248 | 1.53 | 89.6 | 5.7 | 4.8 |
| | 2.5% Pd/ | 230 | 0.86 | 93.9 | 2.8 | 3.2 |
| | 5% Re/HSAG | 218 | 0.64 | 95.3 | 2.1 | 2.6 |
| | | 204 | 0.34 | 96.9 | 1.1 | 2.0 |
| J | 1% Cu/ | 245 | 1.04 | 92.7 | 2.8 | 3.6 |
| | 2.5% Pd/ | 230 | 0.72 | 94.7 | 1.9 | 3.4 |
| | 5% Re/HSAG | 212 | 0.43 | 96.0 | 1.3 | 2.8 |
| | | 191 | 0.22 | 96.9 | 0.8 | 2.3 |
| L | 1.7% Au/ | 249 | 1.65 | 89.9 | 4.3 | 5.8 |
| | 2.5% Pd/ | 231 | 1.11 | 93.3 | 2.7 | 4.1 |
| | 5% Re/HSAG | 214 | 0.67 | 95.2 | 1.7 | 3.2 |
| | | 195 | 0.37 | 96.6 | 1.1 | 2.3 |
| M | 0.5% Ag/ | 250 | 1.29 | 89.3 | 5.9 | 4.8 |
| | 2.5% Pd/ | 230 | 0.84 | 93.6 | 3.2 | 3.2 |
| | 5% Re/HSAG | 218 | 0.54 | 95.0 | 2.3 | 2.7 |
| | | 198 | 0.26 | 96.4 | 1.5 | 2.2 |

Figure 3:
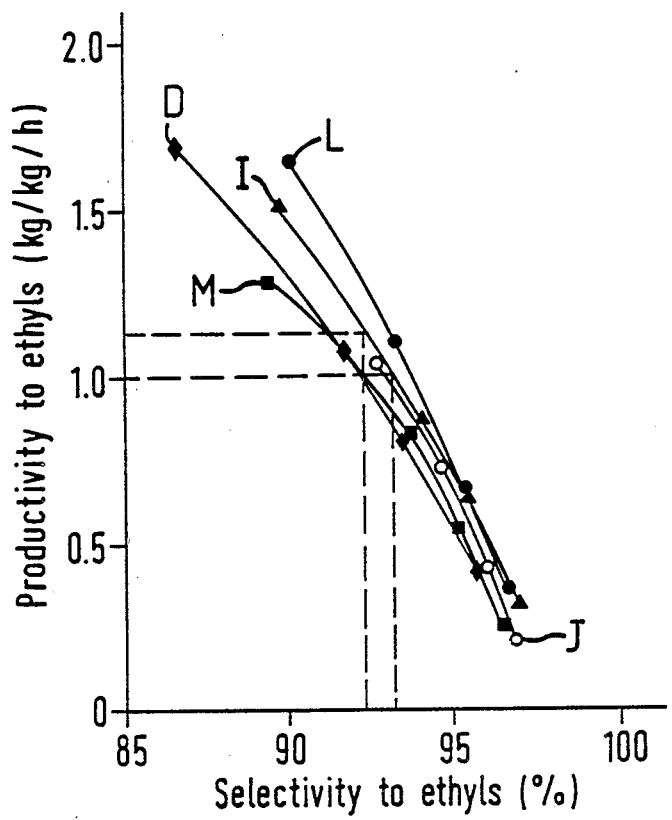
Figure 4:
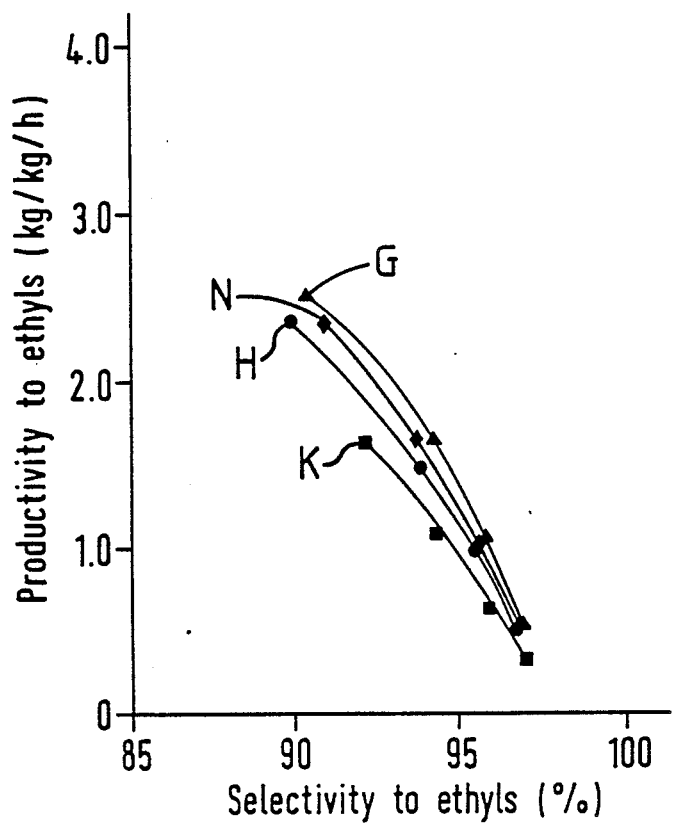

The results provided in Table 5 are presented in graphical form in FIG. 3. It can be seen that in the case of copper the selectivity improvements were greater than for silver, the methane selectivity was reduced by at least 55% and ethane selectivity was reduced by 15% but the concomitant decrease in productivity was also greater. Thus, there was less overall benefit from alloying with copper compared with silver. It can been seen from FIG. 3 that at a productivity of 1.0 kg/kg catalyst/h the selectivity improves from 92% to 93%.

Gold behaves in a similar way to silver.

Alloying with nickel increases the selectivity.

EXAMPLES 40 to 43

The procedure of Examples 12 to 15 was repeated except that instead of Catalyst B of Example 2 there was used Catalyst G of Example 5.

The results are Presented in Table 6.

EXAMPLES 44 to 47

The procedure of Examples 12 to 15 was repeated except that instead of Catalyst B of Example 2 there was used Catalyst H of Example 6.

The results are presented in Table 6.

EXAMPLES 48 to 51

The procedure of Examples 12 to 15 was repeated except that instead of Catalyst B of Example 2 there was used Catalyst K of Example 9.

The results are presented in Table 6.

COMPARISON TESTS 12 to 15

The procedure of Examples 12 to 15 was repeated except that instead of Catalyst B of Example 2 there was used Catalyst N of Comparison Test 3.

The results are presented in Table 6.

at 600° C. followed by cooling to room temperature in nitrogen.

EXAMPLE 53

Catalyst R

The procedure of Example 52 was repeated to give a composition of nominal loading: 3% Pd - 3.07% Ag - 3% Re.

EXAMPLE 54

Catalyst S

The procedure of Example 52 was repeated to give a composition of nominal loading 3% Pd - 6.14 Ag - 3% Re.

TABLE 6

THE EFFECT OF ALLOYING ON CATALYSTS WITH A LOW PALLADIUM LOADING (1.25%) AND A HIGH RHENIUM LOADING (10%)

| Catalyst | Nominal Catalyst Composition | Temperature (°C.) | Productivity to Ethyls (kg/kg/h) | Selectivity (%) | | |
|---|---|---|---|---|---|---|
| | | | | Ethyls | Methane | Ethane |
| E | 1.25% Pd/ | 246 | 2.34 | 90.8 | 3.8 | 5.0 |
| | 10% Re/HSAG | 231 | 1.65 | 93.6 | 2.2 | 4.1 |
| | | 212 | 1.01 | 95.4 | 1.5 | 3.2 |
| | | 190 | 0.54 | 96.7 | 0.8 | 2.5 |
| G | 1.7% Ag/ | 251 | 2.52 | 90.1 | 3.0 | 7.0 |
| | 1.25% Pd/ | 231 | 1.64 | 94.0 | 1.6 | 4.4 |
| | 10% Re/HSAG | 214 | 1.09 | 95.6 | 1.1 | 3.3 |
| | | 196 | 0.52 | 96.8 | 0.7 | 2.5 |
| H | 1.7% Ag/ | 253 | 2.36 | 89.6 | 3.3 | 7.2 |
| | 1.25% Pd/ | 230 | 1.43 | 93.7 | 1.7 | 4.7 |
| | 10% Re/HSAG | 212 | 0.97 | 95.3 | 1.2 | 3.7 |
| | | 191 | 0.49 | 96.7 | 0.8 | 2.6 |
| K | 0.5% Au/ | 245 | 1.64 | 91.9 | 2.2 | 5.9 |
| | 1.25% Pd/ | 230 | 1.09 | 94.1 | 1.5 | 4.4 |
| | 10% Re/HSAG | 212 | 0.64 | 95.7 | 1.0 | 3.3 |
| | | 190 | 0.32 | 96.9 | 0.7 | 2.4 |

(II) Hydrogenation of maleic acid and maleic anhydride

Catalyst Preparation

Hereinafter nominal loading is defined as weight of metal (not salt) added to the support expressed as a percentage of the weight of support.

Comparison Test 16 - Catalyst P

An aqueous solution containing dissolved palladium nitrate was added to HSAG. The water was removed on a rotary evaporator, and the resulting impregnated carbon was dried at 150° C. in an oven overnight. The amount of palladium nitrate was chosen to give a nominal loading of 3% Pd. The catalyst was then cooled and transferred to a glass tube, and was heated in a stream of nitrogen using the following conditions: from room temperature to 300° C. over a period of eight hours then eight hours at 300° C. followed by cooling to room temperature in nitrogen.

This composition was then mixed with an aqueous solution of rhenium heptoxide, the solvent again removed on a rotary evaporator, and the composition dried overnight in an oven at 150° C. to give a catalyst of nominal loading —3% Pd —3% Re.

EXAMPLE 52

Catalyst Q

The procedure of Comparison Test 16 was repeated except that silver nitrate was added to the solution of palladium nitrate. The amounts of the various components were chosen to give a composition with nominal loadings as follows 1.54% Ag, 3% Pd, 3% Re. A second difference was that the composition before the addition of rhenium was heated in a stream of nitrogen using the following conditions: from room temperature to 600° C. over a period of eight hours, then eight hours Catalyst Testing (i) General Method Batch Reactions Comparison Test 17 and 18 and Examples 55 to 60

A 300 ml stainless steel autoclave was purged with nitrogen and then charged with catalyst (usually 1.0 g) and appropriate solution. For the anhydride hydrogenation this consisted of 20 g maleic anhydride dissolved in 120 g 1,4-dioxane. For maleic acid hydrogenation this consisted of 20 g maleic anhydride in 120 g de-ionised water. The autoclave was then purged using hydrogen and then pressurised to 80 barg with hydrogen. Heating and stirring was commenced (5° C./min, 1000 rpm) until 230° C. was attained. This temperature was maintained for twelve hours with continued stirring. After this period the heating/stirring was ceased and the autoclave allowed to cool to room temperature. Gas and liquid phases were sampled and analysed by gas-liquid chromatography. Results are given in Tables 7 and 8.

(ii) Continuous Studies

Comparison Test 19 and Example 61

Continuous testing of catalysts for maleic acid hydrogenation (13 wt % maleic anhydride in de-ionised water) was carried out using a 0.1 dm$^3$ semi-technical unit. For experiments at 725 psig, 100 mls of catalyst was loaded into a stainless steel reactor of internal diameter 25 mm which could be heated in three separate zones (top, catalyst bed, bottom). The catalyst was then activated by heating at 500 psig in a 50:50 stream of H$_2$:N$_2$ to 280° C., at a rate of 15° C./hr, and then holding for six hours. After activation, the catalyst was cooled in hydrogen to the desired reaction temperature. A mixture of maleic acid liquid and hydrogen was then passed over the catalyst, and pressure was adjusted to the required value by means of an air operated automatic pressure control valve.

Catalyst performance was assessed by carrying out 10 hour mass balances preceded by 10 hour pre-runs to allow steady-state condition to be attained. Product vapours, gases and liquid were sampled, after gas/liquid separation, and analysed by off-line gas-liquid chromatography. The temperatures were measured by means of thermocouples inserted into the top, middle and bottom of the catalyst bed. Results ar in Table 9.

TABLE 9-continued

| Conditions: | $H_2$: maleic acid = 60:1 |
|---|---|

*Temperature variation due to reaction
Abbreviations:
THF - tetrahydrofuran
γBLO - gamma-butyrolactone
BDO - 1,4-butane diol Comparison Test 20

The procedure of Examples 55 to 60 for maleic anhydride hydrogenation was repeated except that the catalyst was 3% Pd supported on alumina prepared in the manner of the 3% Pd/HSAG intermediate of Comparison Test 16.

The results are presented in Table 10.

EXAMPLE 62

Comparison Test 20 was repeated except that instead of the 3% Pd/Al$_2$O$_3$ catalyst there was used a 3% Pd/6% Ag/Al$_2$O$_3$ catalyst, prepared in a similar manner (omitting rhenium) to catalyst Q of Example 52.

The results are presented in Table 10.

EXAMPLE 63

Comparison Test 20 was repeated except that instead of the 3% Pd/Al$_2$O$_3$ catalyst there was used a 3% Pd/6% Ag/3% Re/Al$_2$O$_3$ catalyst prepared in the manner of catalyst Q of Example 52.

The results are presented in Table 10.

TABLE 7

EFFECT OF ALLOYING WITH Ag ON MA HYDROGENATION/AQUEOUS SYSTEM

| Ex | Catalyst | Ag Loading | Pd:Ag Ratio | Productivity[1] Kg/kgcat/h | Selectivity (%) γBLO,BDO,THF | Selectivity (%) γBLO | THF | BDO | BuOH | Methane |
|---|---|---|---|---|---|---|---|---|---|---|
| CT17 | P | 0 | — | 0.24 | 97.2 | 95.9 | <0.6% | 1.3 | 0.4 | 1.87 |
| 54 | Q | 1.54% | 1:0.5 | 0.66 | 99.6 | 91.0 | 7.6 | 1.0 | 0 | 0.3 |
| 55 | R | 3.07% | 1:1 | 0.33 | 100 | 96.5 | 1.7 | 1.8 | 0 | 0 |
| 56 | S | 6.14% | 1:2 | 0.27 | 99.3 | 98.1 | 1.2 | 0.7 | 0 | 0.1 |

[1]Productivity to BLO, BDO and THF
Abbreviations:
γBLO - gamma butyrolactone
THF - tetrahydrofuran
BDO - 1,4-butane diol

TABLE 8

EFFECT OF ALLOYING WITH Ag ON MA HYDROGENATION (NON-AQUEOUS SYSTEM)

| Ex | Catalyst | Ag Loading | Pd:Ag Ratio | Productivity[1] Kg/kgcat/h | Selectivity (%) γBLO,BDO,THF | Selectivity (%) γBLO | THF | BDO | BuOH | Methane |
|---|---|---|---|---|---|---|---|---|---|---|
| CT18 | P | 0 | — | 1.19 | 97.8 | 88.9 | 7.6 | 1.3 | 0.4 | 1.8 |
| 58 | Q | 1.54% | 1:0.5 | 0.89 | 99.0 | 95.9 | 1.8 | 1.3 | 0.9 | 0 |
| 59 | R | 3.07% | 1:1 | 0.92 | 98.6 | 94.9 | 2.1 | 1.6 | 1.1 | 0.3 |
| 60 | S | 6.14% | 1:2 | 0.97 | 99.4 | 96.4 | 2.1 | 0.9 | 0.5 | 0.1 |

[1]Productivity to BLO, BDO and THF
Abbreviations:
γBLO - gamma butyrolactone
THF - tetrahydrofuran
BDO - 1,4-butane diol

TABLE 9

| Catalyst | 3% Pd-03% Re/HSAG (P) | 3% Pd-3% Ag-3% HSAG (R) |
|---|---|---|
| Example | CT 19 | 61 |
| Temperature/°C. | 200–260* | 250–260* |
| Conversion | 95% | 93% |
| Productivity (kg/kgcat/h) | 0.34 | 0.33 |
| Product Selectivity % | | |
| Methane | 11 | 0 |
| Alcohols (BuOH + PrOH) | 46 | 2 |
| THF | 2 | 6 |
| γ-BLO | 36 | 89 |
| BDO | 5 | 1 |
| Succinic Acid | — | 2 |

LHSV = 1, GHSV = 2000, P = 725 psig

TABLE 10

| Example | Productivity (kg/kgcat/h) | Selectivity to total C$_4$ Solvents (%) | Selectivity (%) Methane | OH | Total Conversion (%) |
|---|---|---|---|---|---|
| CT20 | 0.85 | 99.6 | 0.2 | 0.2 | 50 |
| 62 | 1.52 | 99.7 | 0.0 | 0.3 | 92 |
| 63 | 1.49 | 98.6 | 0.1 | 1.3 | 91 |

Comparison Test 21

The procedure of Examples 55 to 60 for maleic acid hydrogenation was repeated except that the catalyst was 3% Pd supported on alumina prepared in similar manner to the 3% Pd/HSAG intermediate of Comparison Test 16.

The results are presented in Table 11.

EXAMPLE 64

Comparison Test 21 was repeated except that instead of the 3% Pd/Al$_2$O$_3$ catalyst there was used a 3% Pd/6% Ag/Al$_2$O$_3$ catalyst prepared in a similar manner (omitting rhenium) to catalyst Q of Example 52.

The results are presented in Table 11.

EXAMPLE 65

Comparison Test 21 was repeated except that instead of the 3% Pd/Al$_2$O$_3$ catalyst there was used a 3% Pd/6% Ag/3% Re/Al$_2$O$_3$ catalyst prepared in the manner of catalyst R of Example 53.

The results are prepared in Table 11.

TABLE 11

| Example | Productivity (kg/kgcat/h) | Selectivity to total C$_4$ Solvents (%) | Selectivity (%) Methane | OH | Total Conversion (%) |
|---|---|---|---|---|---|
| CT21 | 0.4 | 97.7 | 1.9 | 0.4 | 14+ |
| 64 | 0.38 | 99.6 | 0.3 | 0.1 | 23 |
| 65 | 0.54 | 99.0 | 0.4 | 0.6 | 32 |

CATALYST PREPARATION - RUTHENIUM BASED CATALYSTS

Comparison Test 22 - Catalyst T

HSAG(5 g) was impregnated with Ru(NO)(NO$_3$) solution (7.3 wt % Ru)(1.61 g) diluted to 50 ml with distilled water. The solution was rotary evaporated to dryness at 70° C. and −800 mbar pressure. The sample was then dried in a vacuum oven at 120° C. for 16 hours prior to reduction at 300° C. under a stream of flowing hydrogen at 1 atm. pressure for 4 hours. The gas flow was switched to nitrogen and the catalyst allowed to cool under this gas. The now ruthenised graphite was impregnated with an aqueous solution (50 ml) containing Re$_2$O$_7$ (0.65 g) and evaporated to dryness at 70° C. and −800 mbar pressure prior to drying for 16 hours in a vacuum oven at 120° C. Nominal catalyst loading:

2.35 wt % Ru-5 wt % Re/HSAG

EXAMPLE 66

Catalyst U

HSAG (5 g) was coimpregnated with Ru(NO)(CO$_3$)$_3$ solution (7.3 wt % Ru)(1.61 g) and Fe(NO$_3$)$_3$.9H$_2$O (0.47 g) in distilled water (100 ml). The solution was rotary evaporated to dryness and dried in a vacuum oven as for Catalyst T. The sample was then reduced as for Catalyst T however, on switching the gas flow to nitrogen the sample temperature was elevated to 800° C. The sample was allowed to cool under flowing nitrogen. Re$_2$O$_7$ was impregnated on to the sample in the same manner as for Catalyst T. Nominal catalyst loading:

2.35 wt % Ru-1.3 wt % Fe-5 wt % Re/HSAG

EXAMPLE 67

Catalyst

This catalyst was prepared in the same manner as Catalyst U except that CO(NO$_3$)$_2$. 6H$_2$O (0.30 g) was used instead of Fe(NO$_3$)$_3$.9H$_2$O. Nominal catalyst loading:

2.35 wt % Ru-1.2 wt % Co-5 wt % Re/HSAG

EXAMPLE 69

Catalyst X

This catalyst was prepared in the same manner as Catalyst V except that only 0.15 g of the cobalt salt was used in the coimpregnation step with ruthenium. Nominal catalyst loading:

2.35 wt % Ru-0.60 wt % Co-5 wt % Re/HSAG

XRD Analysis of the Alloyed Catalysts

All the samples examined showed unalloyed second metal (iron or cobalt) but none provided any evidence for the presence of unalloyed ruthenium. All the samples, i.e. catalysts U,V, W and X also showed significant amounts of unidentified crystalline material. Little information would appear to be available in the literature on XRD studies of Ru-Fe and Ru-Co alloys. However, since the ruthenium content of these catalysts, in atomic terms, is always at least equal to that of the second metal, it would appear likely that the unidentified material is a ruthenium rich Ru-Fe or Ru-Co alloy.

Catalyst Testing

Hydrozenation of acetic acid
Procedure

Reactions were carried out in a single pass plug flow microreactor employing a 2.5 ml catalyst charge. Total reactant pressure was maintained at 10 barg. LHSv was approx 1.35 and the ratio of hydrogen to acetic acid was 10:1. Reaction products were analysed by gc employing both flame ionisation detection and thermal conductivity detection.

Results were obtained at three different temperatures, viz. about 230° C., about 210° C. and about 190° C.

Comparison Test 23

Catalyst T was used in the procedure above.
The results are given in Table 12.

EXAMPLES 70–73

Catalysts U, V, W and X were used in the procedure above.

The results are given in Table 12.

TABLE 12

| Catalyst | T | U | V | W | X |
|---|---|---|---|---|---|
| Actual Temp. (°C.) | 234 | 233 | 235 | 230 | 230 |
| Conversion (%) | 41.32 | 55.40 | 56.67 | 43.46 | 36.08 |
| Sel. (CH$_4$) (%) | 33.04 | 16.89 | 14.21 | 18.80 | 12.85 |
| Sel. (C$_2$H$_6$) (%) | 14.19 | 7.77 | 7.11 | 9.18 | 6.99 |
| Sel. (EtOH) (%) | 47.80 | 54.83 | 64.80 | 62.07 | 71.90 |

TABLE 12-continued

| Catalyst | T | U | V | W | X |
|---|---|---|---|---|---|
| Sel. (EtOAc) (%) | 4.34 | 18.03 | 13.28 | 8.42 | 7.45 |
| Actual Temp. (°C.) | 215 | 210 | 215 | 210 | 210 |
| Conversion (%) | 26.01 | 32.05 | 32.21 | 27.14 | 25.26 |
| Sel. (CH$_4$) (%) | 26.25 | 11.42 | 8.03 | 13.64 | 9.66 |
| Sel. (C$_2$H$_6$) (%) | 11.28 | 6.25 | 4.88 | 7.61 | 5.63 |
| Sel. (EtOH) (%) | 57.25 | 66.30 | 68.51 | 70.65 | 67.29 |
| Sel. (EtOAc) (%) | 4.81 | 11.45 | 18.19 | 6.40 | 15.72 |
| Actual Temp. (°C.) | 194 | 191 | 192 | 195 | 192 |
| Conversion (%) | 14.45 | 19.99 | 13.52 | 19.41 | 14.91 |
| Sel. (CH$_4$) (%) | 18.79 | 7.80 | 6.40 | 10.69 | 5.61 |
| Sel. (C$_2$H$_6$) (%) | 8.96 | 4.87 | 4.79 | 6.39 | 4.05 |
| Sel. (EtOH) (%) | 66.83 | 72.02 | 77.01 | 40.83 | 63.85 |
| Sel. (EtOAc) (%) | 4.91 | 9.67 | 10.58 | 40.24 | 23.74 |

We claim:

1. A process for the production from either a carboxylic acid or an anhydride thereof of the corresponding alcohol and/or carboxylic acid ester which process comprises reacting the carboxylic acid or anhydride thereof with hydrogen at elevated temperature in the presence as catalyst of a composition comprising an alloy of (i) at least one noble metal of Group VIII of the Periodic Table of the Elements, and (ii) at least one metal capable of alloying with the aforesaid Group VIII noble metal.

2. A process according to claim 1 wherein the noble metal of Group VIII is either palladium, rhodium or ruthenium.

3. A process according to claim 1 wherein the noble metal is palladium and the metal capable of alloying with the noble metal is either silver, gold or copper.

4. A process according to claim 1 or claim 2 wherein the catalyst incorporates at least one of the metals rhenium, tungsten or molybdenum.

5. A process according to claim 1 or claim 2 wherein the catalyst composition is supported on either a high surface area graphitised carbon, a graphite, an activated carbon, a silica, an alumina or a silica/alumina.

6. A process according to claim 1 or claim 2 wherein the catalyst comprises (i) an alloy of palladium and silver and (ii) rhenium supported on a high surface area graphitised carbon.

7. A process according to claim 1 or claim 2 wherein there is employed either a carboxylic acid which has the formula R—COOH wherein R is a C$_1$ to C$_{12}$ alkyl group or an anhydride thereof.

8. A process according to claim 7 wherein there is employed a carboxylic acid which is either acetic acid, propionic acid, butyric acid or heptanoic acid.

9. A process according to claim 1 or claim 2 wherein there is employed a saturated or unsaturated dicarboxylic acid or an anhydride thereof.

10. A process according to claim 9 wherein there is employed either a saturated or unsaturated dicarboxylic acid or an anhydride thereof which is either glutaric acid, glutaric anhydride, adipic acid, adipic anhydride, succinic acid, succinic anhydride, maleic acid or maleic anhydride.

11. A process for the production of gamma-butyrolactone from either maleic acid or maleic anhydride which process comprises reacting either maleic acid or maleic anhydride at elevated temperature with hydrogen in the presence as catalyst of a composition comprising an alloy (i) of at least one noble metal of Group VIII of the Periodic Table of the Elements and (ii) at least one metal capable of alloying with the noble metal.

12. A process according to claim 11 wherein the noble metal is either palladium, rhodium or ruthenium.

13. A process according to claim 12 wherein the noble metal is palladium and the metal capable of alloying with the noble metal is either silver, gold or copper.

14. A process according to claim 13 wherein the metal capable of alloying with palladium is silver.

15. A process according to claim 11 or claim 12 wherein the catalyst composition incorporates a support which is either a high surface area graphitised carbon, a graphite, an activated carbon, a silica, an alumina or a silica/alumina.

16. A process according to claim 15 wherein the support is a high surface area graphitised carbon.

17. A process according to claim 11 or claim 12 wherein the maleic acid or maleic anhydride is introduced as a solution.

18. A process according to claim 1, claim 2, claim 11 or claim 12 wherein the catalyst is activated before use in the process.

* * * * *

UNITED STATES PATENT AND TRADEMARK OFFICE
CERTIFICATE OF CORRECTION

PATENT NO. : 4,985,572
DATED : January 15, 1991
INVENTOR(S) : MELANIE KITSON et al It is certified that error appears in the above-identified patent and that said Letters Patent is hereby corrected as shown below:

Col. 2, l. 5, correct the spelling of the word "methane"

Col. 2, l. 9, correct the spelling of the word "use"

Col. 2, l. 43, correct the spelling of the word "aforesaid"

Col. 2, l. 55, should read "to be designated"

Col. 3, l. 9, should read "Brunauer Emmett and Teller"

Col. 3, l. 16, correct the spelling of the word "n-heptane"

Col. 3, l. 41, correct the spelling of the word "form"

Col. 3, l. 43, correct the spelling of the word "use"

Col. 4, l. 48, correct the spelling of the word "least"

Col. 5, l. 56, there should be a comma (,) after the word "silver,"

Col. 6, l. 7, should read "a moving bed or a"

Col. 6, lines 37 and 38, correct the spelling of the word "maleic"

Col. 6, l. 60, should read "with or without the here-"

Col. 7, l. 5, correct the spelling of the word "maleic"

Col. 7, l. 13, should read (LHSV)

Col. 8, l. 36-37, place a colon (:) after "follows:"

Col. 8, l. 49, should read "normal loading:-2.5%"

UNITED STATES PATENT AND TRADEMARK OFFICE
CERTIFICATE OF CORRECTION

PATENT NO. : 4,985,572

DATED : January 15, 1991

INVENTOR(S) : MELANIE KITSON et al

It is certified that error appears in the above-identified patent and that said Letters Patent is hereby corrected as shown below:

Col. 8, l. 66, there should be a dash (-) after the word "follows:"

Col. 10, l. 2, should read "Re/HSAG"

Col. 12, l. 38, in respect of Catalyst G, remove the + sign to the next "silver metal" and insert it before "silver metal"

Col. 12, l. 42, in respect of Catalyst H, remove the plus (+) sign and insert it in the next column before "silver"

Col. 12, l. 61, correct the spelling of the word "Hydrogenation"

Col. 13, l. 33, correct the spelling of the word "Space"

Col. 13, l. 35, should read "LHSV"

Col. 13, l. 36, should read "feed per liter of"

Col. 13, l. 45, should read "was ca 10:1 molar,"

Col. 15, l. 43, should read "from 92% to 94% by"

Col. 15, l. 54, should read "used Catalyst I of Example 7" and "EXAMPLE 7" should be deleted on Line 55

Col. 16, l. 18, correct the spelling of the word "presented"

Col. 16, l. 63, correct the spelling of the word "presented"

Col. 19, l. 11, correct the spelling of the word "are"

UNITED STATES PATENT AND TRADEMARK OFFICE
CERTIFICATE OF CORRECTION

PATENT NO. : 4,985,572

DATED : January 15, 1991

INVENTOR(S) : MELANIE KITSON et al

It is certified that error appears in the above-identified patent and that said Letters Patent is hereby corrected as shown below:

Col. 19, l. 57, should read "Conditions: LHSV = 1, GHSV = 2000, P= 725 psig" and appear on line 58

Col. 22, line 43, correct the spelling of the word "Hydrogenation"

Col. 22, l. 47, should read "LHSV was"

Signed and Sealed this

Seventh Day of July, 1992

Attest:

DOUGLAS B. COMER

Attesting Officer

Acting Commissioner of Patents and Trademarks